(12) United States Patent
Sage et al.

(10) Patent No.: US 7,343,206 B2
(45) Date of Patent: Mar. 11, 2008

(54) IMPLANTABLE MEDICAL LEAD AND SYSTEM, AND METHOD OF USE THEREOF

(75) Inventors: Shahn S. Sage, Andover, MN (US); Jose M. Hernandez, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 625 days.

(21) Appl. No.: 10/835,939

(22) Filed: Apr. 30, 2004

(65) Prior Publication Data
US 2005/0021119 A1  Jan. 27, 2005

Related U.S. Application Data

(63) Continuation-in-part of application No. 10/423,179, filed on Apr. 25, 2003, now abandoned.

(51) Int. Cl.
*A61N 1/00* (2006.01)
(52) U.S. Cl. ...................................................... 607/117

(58) Field of Classification Search ................ 607/122, 607/132, 117
See application file for complete search history.

(56) References Cited

U.S. PATENT DOCUMENTS

| | | | | |
|---|---|---|---|---|
| 4,351,345 | A | * | 9/1982 | Carney ........................ 607/122 |
| 5,107,856 | A | * | 4/1992 | Kristiansen et al. ......... 607/126 |
| 6,132,456 | A | * | 10/2000 | Sommer et al. ............. 607/127 |
| 2003/0220677 | A1 | * | 11/2003 | Doan et al. .................. 607/122 |

* cited by examiner

*Primary Examiner*—Scott M. Getzow
(74) *Attorney, Agent, or Firm*—Stephen W. Bauer; Rick L. Franzen

(57) ABSTRACT

Implantable medical leads, lead assemblies, and methods for implanting the leads into the human body, for example, for use within the epidural spaces of the spinal column to manage pain. A stylet lumen extends within the lead between a side-wall stylet entrance port and a lead distal region. In use, exemplary stylets may be inserted through the lead stylet port to stiffen only the distal portion of the lead, and the distal portion of the lead inserted through an introducer needle into the human body. The stiffened distal portion of the lead may be short and easily controllable.

26 Claims, 9 Drawing Sheets

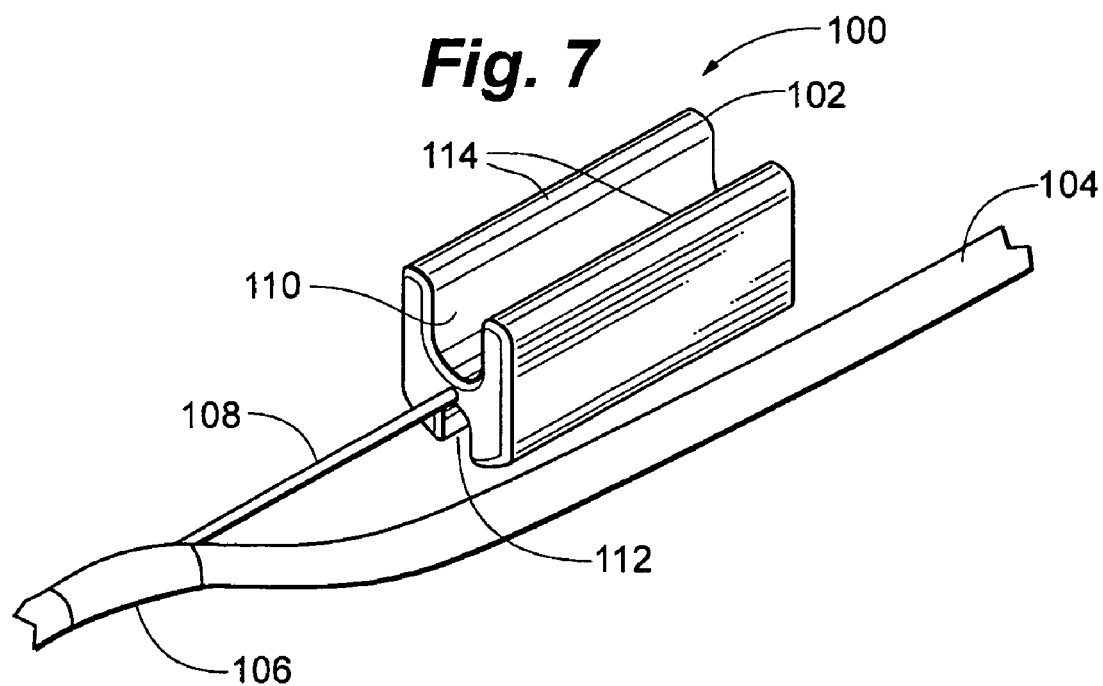
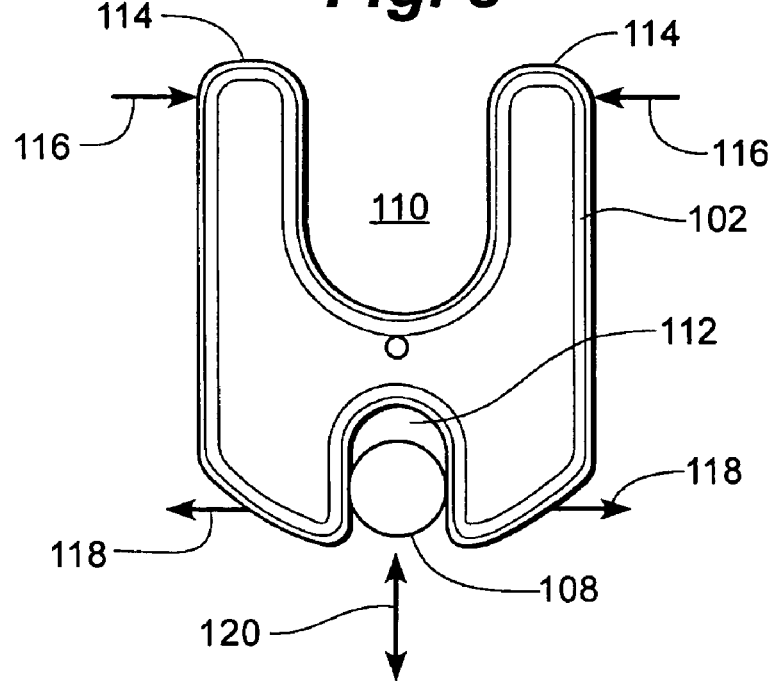

IMPLANTABLE MEDICAL LEAD AND SYSTEM, AND METHOD OF USE THEREOF

RELATED APPLICATIONS

This application is a continuation-in-part of U.S. patent application Ser. No. 10/423,179, filed Apr. 25, 2003, now abandoned, which is incorporated herein by reference in its entirety.

FIELD OF THE INVENTION

This application relates generally to medical leads, and more specifically to implantable, electrical neurological leads.

BACKGROUND OF THE INVENTION

Implantable leads having externally exposed ring or band electrodes can be used to deliver electrical stimulation to surrounding tissue and/or to sense electrical energy produced by the surrounding tissue. Such leads are often implanted, for example, within the epidural or intrathecal spaces of the spinal column, along peripheral nerves, within the brain, and about the heart. Electrical stimulation of the spinal cord has been shown to be effective in relieving intractable pain in some patients. Such electrical stimulation can reduce or eliminate the use of pain relieving drugs.

One such lead is formed of polymeric material, for example, polyurethane or silicone. The lead can be nominally 1 mm in outer diameter and about 20 cm in length. A typical lead may have a series of electrodes formed as bands or rings disposed in a spaced apart relationship in a lead distal region. The distal region of the lead can be introduced, for example, into the epidural region for use in stimulation of the spinal column. The lead proximal region may have a corresponding set of band or ring connectors or terminals, one for each corresponding electrode in the distal region. Each proximal region terminal can thus be connected to one distal electrode in a typical configuration.

The terminals can be used to couple the proximal end of the lead to a lead extension, which can in turn be coupled to an implantable pulse generator (IPG). The lead extension can provide added length to extend the reach of the lead to a more distantly placed IPG. In some embodiments, the lead extension is between about 20 and 50 cm in length.

The lead typically has a lumen extending from the proximal end through to the distal region, with the lumen being dimensioned to accept a stiffening member or stylet. The lead, commonly formed of a polymeric material and being very small in cross section, is typically very floppy and not pushable. With a stylet or stiffening member inserted, the lead gains the needed pushability, and can be advanced into and up the spinal column to the desired location.

In use, a large gauge Toughy needle can be inserted into the spinal column and into the spinal canal. The stylet is then inserted into the lead, and the now stiffened lead advanced through the needle and up into the spinal canal. When the distal region of the lead is in the proper position, the stiffening member can be removed and the introducing needle also removed, leaving the proximal end of the lead protruding from the patient.

A small incision can then be made near the site of entry of the lead, in order to direct the proximal end of the neurological lead back into the body to be mated to a lead extension or to the IPG. The proximal end of the lead extension is coupled to the proximal end of the lead, and electrical continuity established. The lead extension is used to extend the useful length of the lead sufficient to reach the implanted IPG, which can be, for example, 20-50 cm distant. With the length increased by the extension, the free end of the extension can be inserted into the incision and into the body.

In one procedure, known as "tunneling", an elongate, flexible metal device is used to form a tunnel or passageway under the skin, for example, around the torso, to the site of the implanted or soon to be implanted IPG. This tunneling procedure can be used to form the passageway for the extension, which is then advanced through the passageway and to the IPG site.

The extension, while adding length, also adds complexity and cost. It also adds yet another required step for the treating physician to perform. Increasing the lead length to do away with the need for the extension would be desirable. However, with current leads, the stiffening member or stylet would likewise have to be increased in length. While this is possible, a significantly longer lead having a stiffening member within would be somewhat unwieldy. For example, a 50 cm long stylet inserted within a 50 cm long lead would be difficult for the treating physician to maneuver. This aspect is significantly limiting, given that the treatment site is the spinal cord, where care must be exercised.

SUMMARY OF THE INVENTION

Exemplary embodiments of the invention provide (a) neurological stimulating leads that are sufficiently long such that an extension is not required; (b) long neurological leads having distal stiffness and pushability without being unwieldy for the treating physician; or (c) neurological leads that may be provided in a variety of lengths all sharing a common stiffening member (i.e. not requiring a different stiffening member to match each size lead).

An exemplary embodiment includes an implantable lead including a proximal region, a distal region, an intermediate region disposed between the proximal and distal regions, and a side wall. The lead further includes at least one proximal contact and at least one distal contact, electrically coupled to each other by a conductor. The lead includes a lumen disposed through the lead body between the distal region and the intermediate region and a stylet port providing access between the lead body sidewall and the lumen in the intermediate region. The stylet port and lumen can be adapted to slidably receive a stiffening member or stylet through the port and into the lead distal region. Some embodiments of the implantable lead assembly include the implantable lead and a stylet adapted to be slidably received in the implantable lead stylet port and stylet lumen.

Some exemplary lead embodiments have no preformed stylet port to allow access from the lead body exterior to the stylet lumen within. Such leads may require formation of a stylet access port through the lead body sidewall. To avoid inserting the stylet through the conductor, some leads have an indicia of radial position on the lead body. The indicia can indicate a radial position about the lead body at which the insertion of a stylet into the lead body will not sever the conductors. Such indicia can be visible stripes or dots in some embodiments. The indicia can also be a depression or a longitudinal groove formed into the lead body. The indicia can be used to properly position a stylet to be inserted into the lead body, as well as to position an introducer or a hole-forming device properly on the lead body.

Some exemplary implantable lead embodiments have a plurality of distal contacts and a plurality of proximal contacts, with the stylet port disposed between the innermost of the distal and the proximal contacts. Some exemplary leads have a radiopaque marker disposed near the stylet port for locating the stylet port under fluoroscopy. The marker may include a radiopaque seal disposed at least partially in the stylet port. Some leads include a stylet guide disposed about the stylet port, the stylet guide including an aperture for receiving the stylet. Some stylet guides include a stylet guide arm extending radially and distally into the stylet port for distally directing an inserted stylet. The stylet guide can be formed of, and/or plated with, a radiopaque material such as gold or platinum.

An additional exemplary embodiment includes stylet introducers and hole-forming devices to aid in inserting stylets into the lead bodies. One exemplary introducer or hole-forming device includes a body having a sharp inward protrusion to puncture the sidewall of the lead body, forming a port to access the stylet lumen from outside of the lead body. A stylet can then be advanced through a channel, through the introducer sharp inward protrusion, and through a lumen extending through the lead body.

Hole-forming fixtures, guides, or devices can also be used to form a hole at the appropriate radial, longitudinal, and angular position relative to the lead body. One such hole-forming device includes a body having an angled shaft secured to the body, with a channel extending through the shaft and the body. The body can have a longitudinal external channel to fit over the lead body and can also have a downward protrusion or nib to mate to a longitudinal groove in the lead body. The hole-forming device shaft channel can be adapted to receive an elongate, sharp, hole-forming member. The hole-forming device can thus be used to puncture the lead at the appropriate position to form an access port for the stylet to the stylet lumen of the lead body.

Exemplary sealing sleeves may also be provided for sealing the stylet port after the lead body has been appropriately positioned within the patient. The sealing sleeve can include a soft, pliable inner sleeve and a harder, outer sleeve. The sealing sleeves can be disposed over the stylet access port to seal the port. With the sealing sleeve or sleeves in place, suture guides on some sealing sleeves can be used to suture the sleeve into position and secure the sleeve to a known position in the patient.

In use, an exemplary implantable lead having the desired total length and suitable characteristics is selected for implantation. The lead preferably has a stylet lumen extending between the lead side wall stylet port and the lead distal region. The length between the stylet port and the end of the stylet lumen is preferably dimensioned to receive the stylet, regardless of the total lead length. An introducer needle can be advanced into the body near the implantation site. The stiffening member or stylet can be inserted into the lead stylet port and further distally into the lead to stiffen the lead distal region. The stiffened lead can be inserted through the lumen of the introducer needle and further distally from the needle to the target site. The stylet can be retracted from the lead, and the introducer needle retracted as well, leaving the lead proximal region extending from the body. In some methods, the lead proximal end is coupled to a lead extension before being tunneled into the body to fully implant the lead.

With the lead positioned and the stylet retracted from the lead, the stylet port of certain exemplary embodiments may be sealed using a sealant or a curable adhesive. In some exemplary methods, a sealing sleeve or sleeves is either longitudinally slid over the stylet port or transversely applied over the port. Some sealing sleeves are at least partially radiopaque to indicate the position of the sleeve under fluoroscopy.

Exemplary embodiments of the lead, lead assembly, and lead implantation methods allow for implanting a variety of lead lengths while stiffening only the lead distal portion. The lead portion disposed proximal of the stylet port need not be stiffened and/or include a stylet lumen within. This remaining lead proximal portion can be sufficiently long to eliminate the need for a lead extension by not requiring that the entire lead length accept a stylet to provide for stiffening. A single length stylet may thus be used with a family of leads, each having a different total length, but having a similar length stylet lumen within.

BRIEF DESCRIPTION OF THE DRAWINGS

FIG. 7 is a fragmentary, perspective view of an assembly having a stylet handle adapted to grip a neurological lead;

FIG. 8 is a transverse, cross-sectional view of the handle of FIG. 7, having the lead held within the longitudinal channel;

DETAILED DESCRIPTION OF EXEMPLARY EMBODIMENTS

Figure 1:
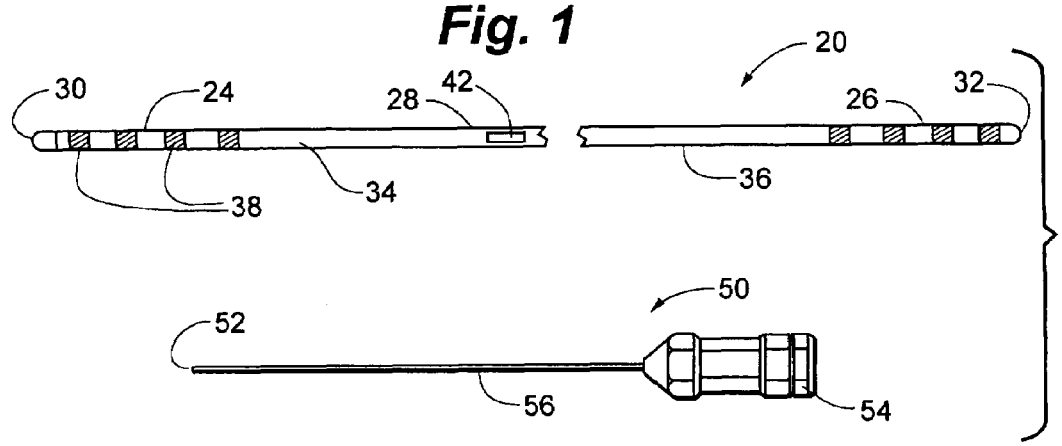
FIG. 1 is a side view of an implantable lead having an intermediate stylet insertion port and a stylet for insertion into the port.

FIG. 1 illustrates a neurological stimulation lead 20 having a distal region 24, a proximal region 26, and an immediate region 28 disposed between the distal and proximal regions. In a preferred embodiment, the intermediate region is defined to lie between the innermost distal and proximal electrical contacts described below. A stylet entrance or insertion part 42 may be seen in intermediate region 28. Lead 20 can be formed of a body or shaft 34 extending between a distal end 30 and a proximal end 32. Lead body 34 has an exterior surface or tubular side wall 36. Lead body 34 is preferably formed of a polymeric material, for example, polyurethane or silicone.

Lead distal region 24 may include a number of electrodes 38, which may, for example, be disposed concentrically about lead body 34 in a spaced-apart configuration. Electrodes 38 may also be described as electrical contacts or contacts. Electrodes 38 are normally adapted to be inserted into the human body, are externally exposed, and can be used for neurological stimulation. One exemplary use of electrodes 38 is the stimulation of the nerves within the spinal cord. Proximal region 26 can include a number of connector bands or connector rings 40 disposed in a spaced-apart configuration. Connectors 40 may also be described as electrical contacts or terminals, and are preferably also externally exposed. Electrodes 38 and connectors 40 may be formed of Platinum and/or Iridium. Connectors 40 can be used for connecting lead 20 to a lead extension to extend the effective length of the lead. In some uses, connectors 40 may also be used to directly couple lead 22 to an implantable pulse generator.

Electrodes 38 and connectors 40 can be coupled to each other in a one-to-one arrangement. In some leads, the distal-most electrode is coupled to the distal-most connector, the second-to-distal-most electrode coupled to the second-to-distal-most connector, and so forth. The electrodes and connectors can be coupled through conductors extending between the two. In some leads, the conductors are embedded within the lead while in other leads, the conductors lie within lumens extending the length of the lead. In some leads, the conductors are disposed within lumens that are later backfilled to substantially fill the lumens with a polymeric material.

FIG. 1 also illustrates a stylet 50. Stylet 50 includes generally a shaft 56 extending between a distal tip 52 and a proximal end or handle 54. Stylet 50 is typically dimensioned to be slideably received within stylet entrance 42 and further within a lumen extending distally from stylet entrance 42 toward distal region 24.

Lead 20 can be varied in outer diameter and length to suit the application for which it is intended. In some embodiments, lead 20 has a total length of between about 5 cm and about 100 cm. In other embodiments, lead 20 has an outer diameter of less than about 1 mm and a total length of between about 10 cm and 150 cm. The lead length between stylet entrance 42 and distal end 30 can vary as well. In some embodiments, the distance from stylet entrance 42 to distal end 30 is less than 50 cm, preferably less than 30 cm, and most preferably less than about 20 cm. Stylet 50 preferably has a length adapted to approximately match the length between stylet entrance 42 and distal end 30. Stylet 50 preferably has a shaft outer diameter of less than about 0.050 inches, more preferably less than about 0.020 inches, and most preferably less than about 0.010 inches.

Figure 2:
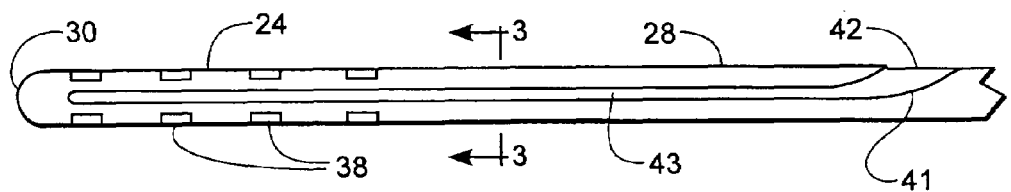
FIG. 2 is a fragmentary, longitudinal cross-sectional view of a distal portion of the lead of FIG. 1.

FIG. 2 illustrates a distal portion of lead 20 in longitudinal cross-section. Lead 20 may be seen to have a flared lumen portion 41 extending from stylet entrance or port 42 toward distal region 24. A stylet lumen 43 may be seen to extend distally from stylet opening 42. In the embodiment illustrated, stylet lumen 43 terminates proximal of lead distal end 30. In some leads, port 42 lies at an angle of between about 20 and 60 degrees from the longitudinal axis of the lead. In one lead embodiment, port 42 lies at an angle of about 30 degrees from the lead longitudinal axis. In other embodiments, port 42 is dimensioned and configured such that a stiffening member inserted into lead 20 to distal region 24 lies at an angle of less than about 40 degrees, preferably about 30 degrees, from the lead longitudinal axis near port 42. Leads preferably have a distal region wall thickness of at least about 0.004 inch. In some leads, a plug material can be disposed within or about stylet port 42 in order to provide a seal between the lead lumen or lumens and the body in which it is inserted. In some leads, a silicone polymeric material carrying a radiopaque marker material is used to plug stylet port 42. In one such plug material, silicone carrying a barium oxide radiopaque material is used as the plug material. The plug or seal material can be inserted into port 42 during manufacture. The stylet distal tip can be advanced through the silicone sealing material to stiffen the lead, and can later be retracted. In some embodiments, radiopaque marker bands can be disposed near one or both sides of stylet port 42 in order to better mark the stylet port for identification of the stylet opening location under fluoroscopy, should surgical access to the port later be required.

Figure 3:
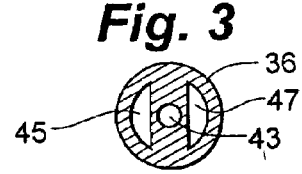
FIG. 3 is a transverse, cross-sectional view taken through 3-3 of FIG. 2, showing a distal tri-lumen portion of the lead.

FIG. 3 illustrates a transverse cross-section taken through a distal portion of lead 20. Lead 20 may be seen to have a tri-lumen configuration in FIG. 3, having a first lumen 45, a second lumen 47, and a third or stylet lumen 43. The tri-lumen configuration can be used to provide lumens for conductors extending between the electrodes and connectors, while separating the conductors from the inserted stylet. The conductors may lie within first and second lumens 45 and 47, leaving lumen 43 clear to receive a stylet. In some leads, a mono-lumen configuration may be found proximal of the stylet opening, where the stylet presence need not be adapted for, leaving a larger cross-sectional area for the conductors.

Figure 4:
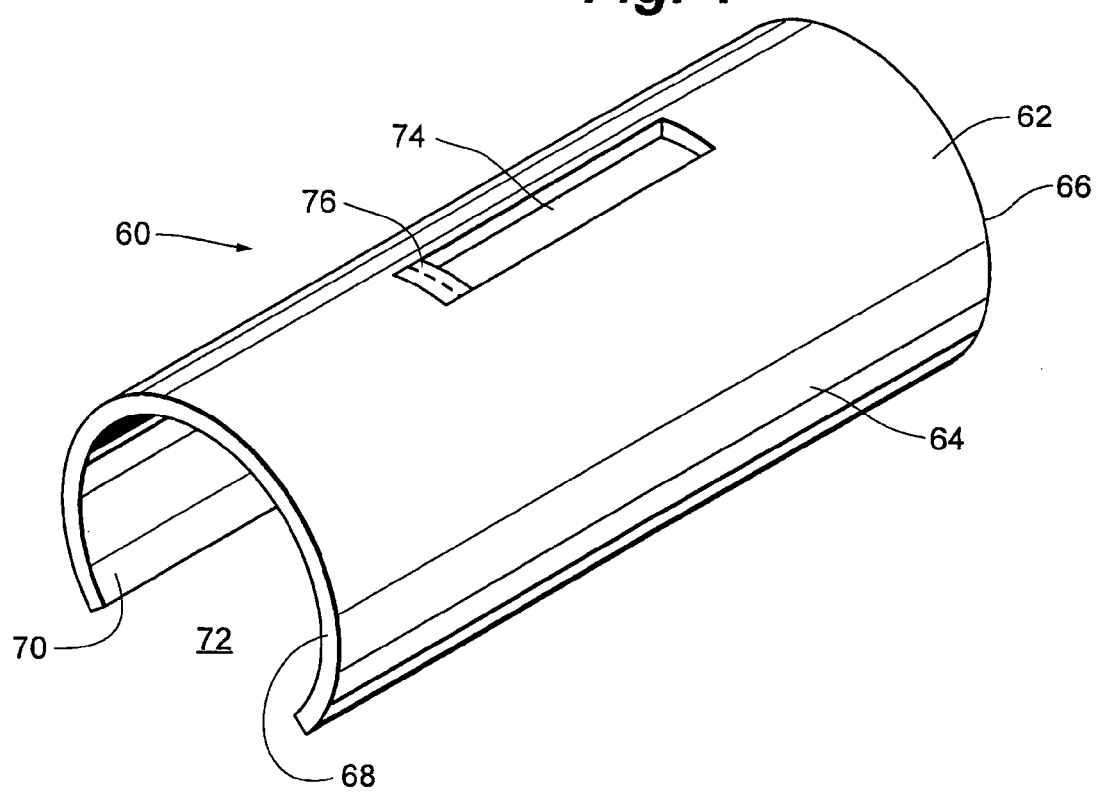
FIG. 4 is a perspective view of a stylet guide or marker that can be positioned over the intermediate insertion port of a lead.

FIG. 4 illustrates a stylet guide or marker 60 for augmenting and marking stylet entrance 42. Stylet guide 60 can be used to both mark the stylet entrance and to aid in proper insertion of the stylet into the lead. Stylet guide 60 may be seen to have generally a distal end 66, a proximal end 68, a substantially cylindrical body 62, an outer surface 64, and an inner surface 70. Cylindrical body 62 may be seen to include a gap 72, an aperture 74, and a deflector arm 76 for properly directing a stylet into the stylet lumen. Stylet guide 60 may be made from sheet metal, for example, stainless steel. The sheet metal may be stamped into the appropriate shape, with aperture 74 being formed through body 62 and deflector arm 76 pushed downward from aperture 74. Stylet guide 60 may then be plated with a radiopaque marker material, for example, gold or platinum.

Figure 5:
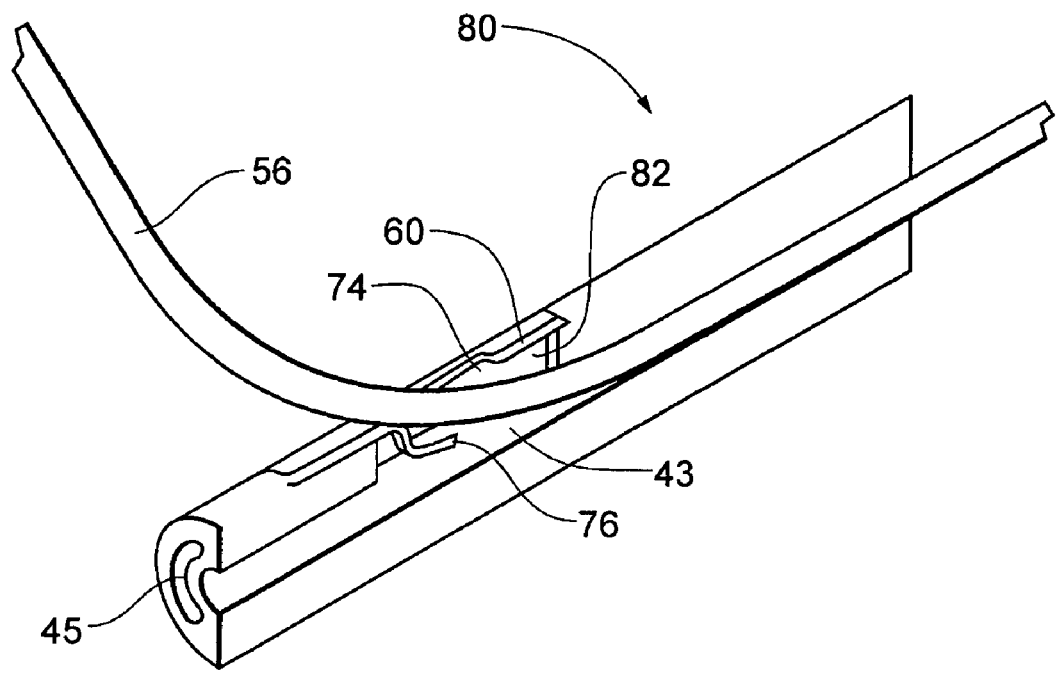
FIG. 5 is a fragmentary, cutaway view of a lead intermediate portion having the stylet marker of FIG. 4 guiding a stylet into the intermediate insertion port.

FIG. 5 illustrates an intermediate portion of another neurological lead 80, similar in many respects to lead 20 of FIG. 1, and sharing some identically numbered features. Lead 80 differs in having a stylet port or opening 82 that is not flared. Lead 80 includes stylet guide or marker 60 of FIG. 4 disposed over and about stylet opening 82. Stylet deflector arm 76 may be seen guiding stylet shaft 56 distally into stylet lumen 43. First conductor lumen 45 may also be seen, previously discussed with respect to FIG. 3. As may be seen from inspection of FIG. 5, deflector arm 76 extends radially inward and distally along stylet guide aperture 74 to ensure that stylet shaft 56 can be inserted in only the distal direction. Stylet guide 60 can also serve to provide a large radiopaque marker easily visible under fluoroscopy.

Figure 6:
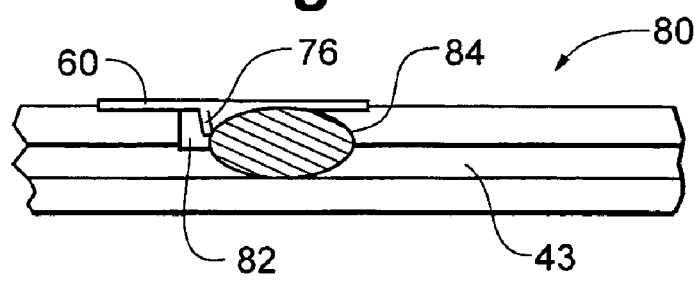
FIG. 6 is a fragmentary, longitudinal, cross-sectional view of the lead intermediate portion of FIG. 5, having a sealing filler material sealing the intermediate insertion port.

FIG. 6 further illustrates lead 80, having a seal or filler material plug 84 disposed within stylet opening 82. Stylet guide 60 and deflector arm 76 may also be seen in FIG. 6. In some methods, seal 84 is injected or placed after withdrawal of the stylet and proper placement of the lead. In a preferred embodiment, seal 84 is injected or otherwise placed within stylet opening 82 during manufacture, with the stylet being inserted through the soft pliable material.

FIG. 7 illustrates an assembly 100 including a stylet wire or shaft 108 coupled to a stylet proximal handle 102 being inserted into a neurological lead 104. Stylet wire 108 is in the process of being advanced into a stylet port (not visible in FIG. 7) in an intermediate portion 106 of lead 104. Stylet handle 102 includes a first, longitudinal channel 112 and a second, longitudinal channel 110. Second longitudinal channel 110 may be seen to be disposed within handles or wings 114. In some embodiments, the first longitudinal channel 112 is dimensioned to firmly grasp and hold lead 104 within.

FIG. 8 illustrates stylet handle 102 having stylet wire 108 held within first longitudinal channel 112. In some embodiments, wings 114 can be squeezed together, as indicated at 116. This squeezing motion can force apart the portions of handle 102 on either side of first longitudinal channel 112, as indicated at 118, thereby increasing the width of first longitudinal channel 112. With the width slightly increased, stylet wire 108 can be more easily transversely forced into first longitudinal channel 112, as indicated at 120. In other embodiments, handle 102 is formed of sufficiently elastic material to allow stylet wire 108 to be forced into, and retrieved from, first channel 112 without squeezing on the opposite side of the handle. In still another embodiment, the stylet handle is formed from a substantially round cross-section, cylindrical, elongate material, having the first, and second channels formed on opposite sides of the elongated cylinder.

Handle 102 can be formed of a polymeric material, for example, a thermoset plastic. In one embodiment, first longitudinal channel 112 has about 0.050 inch width and about a 0.07 to 0.08 inch depth. Second longitudinal channel 110 can have a width of about 0.2 inches and a depth of about 0.25 inches. The handle can have a nominal width of about ⅜ths inch and a length of 0.5 inch. In some embodiments, the handle is formed from a ⅜ths inch outer diameter cylinder, and the channels formed into opposite surfaces of the cylindrical piece.

In use, stylet wire 108 can be advanced into the insertion port in lead 104 until the stylet wire is substantially totally advanced into the lead. The lead can then be transversely forced into the gripping first longitudinal channel, for example, by squeezing opposing wings on the handle. The handle and the lead are now aligned and move as a single unit. In particular, the handle and lead now rotate together. The combined stylet and lead can now be advanced into the introducer needle, as described below with respect to the invention generally.

In use, an introducer needle, for example, a 14 or 16 gauge Toughy needle, may be advanced into the intrathecal space in the spinal column. The stylet may then be advanced distally through the stylet opening to stiffen the lead. The now stiffened lead may be advanced distally through the positioned introducer needle and into the intrathecal space in the spinal column. The lead can be advanced upward through the spinal canal, past the distal tip of the introducer needle. When the lead has been properly positioned, the stylet can be retracted from the lead, and the introducer needle retracted from about the lead. The proximal region of the lead, extending from the body, can be properly coupled to a lead extension or directly to an implantable pulse generator. The free end of the lead or lead extension can also be "tunneled" to an appropriate site within the body for appropriate coupling to an implantable pulse generator.

Referring again to FIG. 1, other aspects of the invention may be further discussed. Inspection of FIG. 1 shows a length between stylet opening 42 and distal end 30 as well as a length between stylet opening 42 and proximal end 32. Different applications and different target sites call for a different total length for lead 20 between distal end 30 and proximal end 32. Different treatments and target sites may also differ as to the length of lead 20 to be inserted into the body.

In previous leads, leads having a different total length required stylets or stiffening members having a corresponding different length to match the lead length. Some exemplary embodiments provide a series of leads, each having a different total length, but allowing for use of the same length stylet. The lead length between the stylet entrance and the distal end of the stylet lumen of each of the various leads in the series is adapted to receive the same stylet. In one example of the invention, a stylet having a length of about 15 cm can be used with each member of a family of varying length leads having a distance from stylet entrance to distal end of about 15 cm. This allows the treating physician to select the appropriate lead while using the same stylet. As previously discussed, exemplary embodiments also provide a lead that is capable of eliminating the need for a lead extension, as the proximal portion can be quite long.

Exemplary embodiments include, for example, a neurological stimulation lead; implantable leads for sensing; implantable leads for both stimulation and sensing, and medical leads for implantation in non-spinal sites, for example, brain and cardiac implantation sites.

Figure 9:
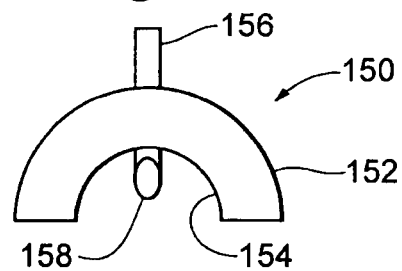
FIG. 9 is an end view of an introducer or hole-forming device for introducing a stylet into the stylet lumen of a lead.

Another exemplary embodiment includes devices for forming an intermediate port, introducing a stylet into the port and sealing the port. FIG. 9 illustrates an introducer 150, which may also be referred to as a hole-forming device or hole-forming guide. Introducer 150 can be used to introduce the stylet into the lead body and into the lead body stylet lumen. Introducer 150 can be adapted to fit closely over a lead body into which the stylet insertion is desired. Introducer 150 includes generally a body 152 having an inner surface 154. Introducer 150 also includes a tube shaft 156 having a sharp distal tip 158.

Figure 10:
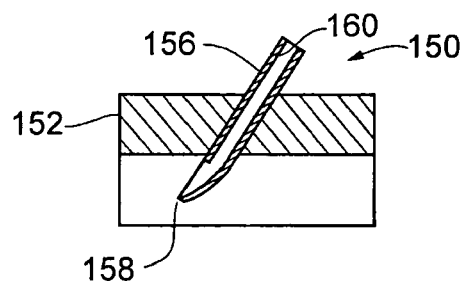
FIG. 10 is a longitudinal, cross-sectional view of the introducer of FIG. 9.

FIG. 10 illustrates introducer 150 of FIG. 9 from a longitudinal cross-sectional view. Introducer 150 may be seen to include a channel 160 within tube 156. In some methods, the distal tip of the introducer is inserted into an existing port in the lead body, and the stylet introduced through the lumen of the introducer body, for example, channel 160 of tube 156 of introducer 150. In other methods, the lead body has no pre-existing port providing access to the stylet lumen within, and the sharp distal tip of the introducer is used to form the port providing access between the sidewall and the inner stylet lumen. In this method, introducer 150 is urged against the lead body at the desired location, and an access port for the stylet is formed into the lead body using sharp distal tip 158. A stylet can then be advanced through the introducer body 150 and into the stylet lumen in the lead. The introducer body may be left in place as the lead portion carrying the stylet is advanced into the body.

Figure 11:
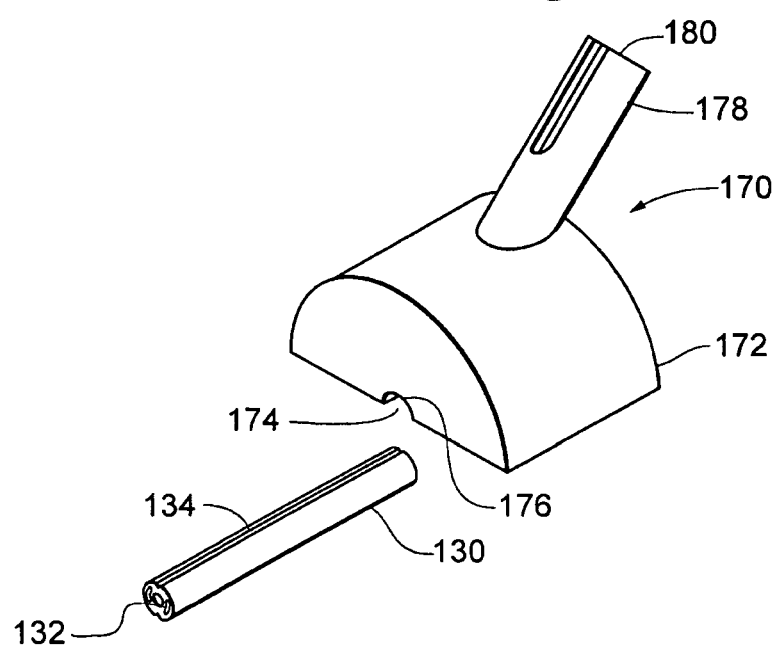
FIG. 11 is a perspective view of a lead body and a hole-forming device or guide for forming a port in the lead body to access the stylet lumen.

FIG. 11 illustrates a lead body section 130 having a central lumen 132 for receiving a stylet as well as a long depression or groove 134. A depression or groove, such as longitudinal groove 134 can serve as an indicia of a radial location about the lead body at which an inserted stylet will not contact one of the conductor lumens or conductors. In some embodiments, a short depression, for example, a small dimple or crater may serve as the indicia of radial position. In other embodiments, a long groove serves as the indicia of radial position. At the indicated radial position, a stylet may be inserted to the lead center, without fear of contacting a conductor within the lead body. Inspection of FIG. 11 indicates that a stylet inserted 90 degrees away from longitudinal groove 134 would likely contact one of the lumens disposed on either side of central lumen 132 (better illustrated in FIG. 16).

FIG. 11 also illustrates an introducer 170, which also may be referred to as a hole-forming device, a hole-forming guide, or a hole-forming fixture. Hole-forming device 170 includes a body 172 having a longitudinal external channel 174 extending along its length, with the longitudinal external channel 174 having a downward protrusion 176 therein. Hole-forming device 170 also includes a guide tube or shaft 178 having a channel or lumen 180 for receiving an elongate sharp member to form the access port in lead body 130.

Figure 12:
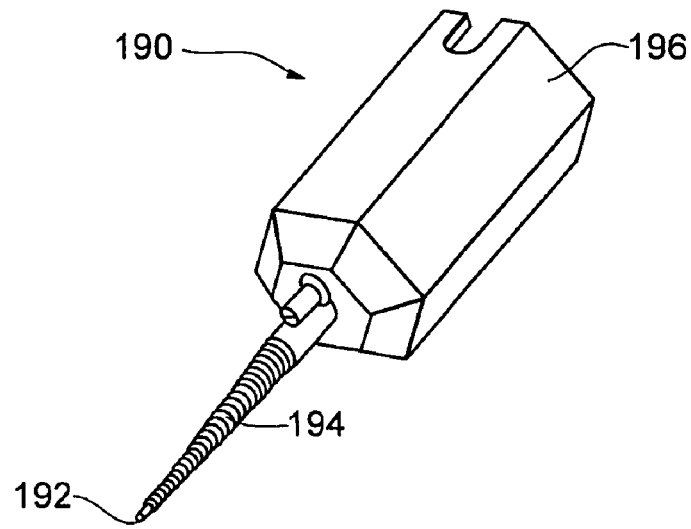
FIG. 12 is a perspective view of an elongate member for forming a hole or port into a lead body to access the lead lumen.

FIG. 12 illustrates an elongate member 190 adapted to be received within hole-forming device 170 of FIG. 11 for forming a hole or port in lead body 130. Elongate member 190 may be seen to include a handle 196, a spring coil distal portion 194, and a sharp distal tip 192 carried by spring coil 194.

Figure 13:
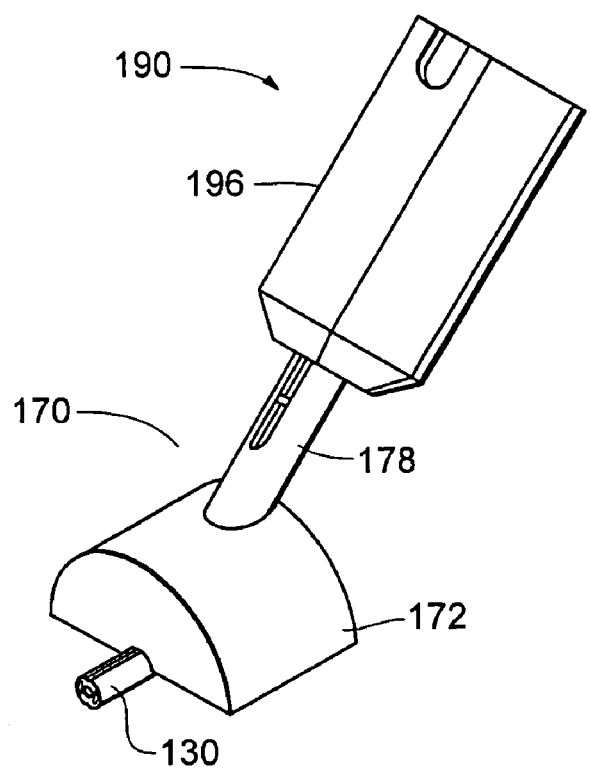
FIG. 13 is a perspective view of the lead and hole-forming device of FIG. 11 having the elongate member of FIG. 12 inserted into the lead to form a port.

FIG. 13 illustrates elongate member 190 of FIG. 12 being received within guide tube 178 of introducer or guide 170. Distal tip 192 can be guided in this way to puncture lead 130 at an appropriate angle and to an appropriate depth. In some embodiments, guide tube 178 is disposed at an angle of between less than 60 degrees or less than 40 degrees from the longitudinal central axis of lead body 130. In use, hole-forming device or introducer 170 can be disposed over lead 130, using longitudinal external channel 174 as a rough positioning device, and downward protrusion 176 as a finer positioning device, for positioning introducer 170 exactly where desired on lead body 130. With introducer 170 in place, elongate member 190 may be advanced through the introducer body, with the distal end of the elongate member puncturing the lead body to form an access port. In some embodiments, introducer 170 can then be removed, together with elongate member 190. A stylet can then be inserted into the lead body stylet lumen through the access port recently formed.

Figure 14:
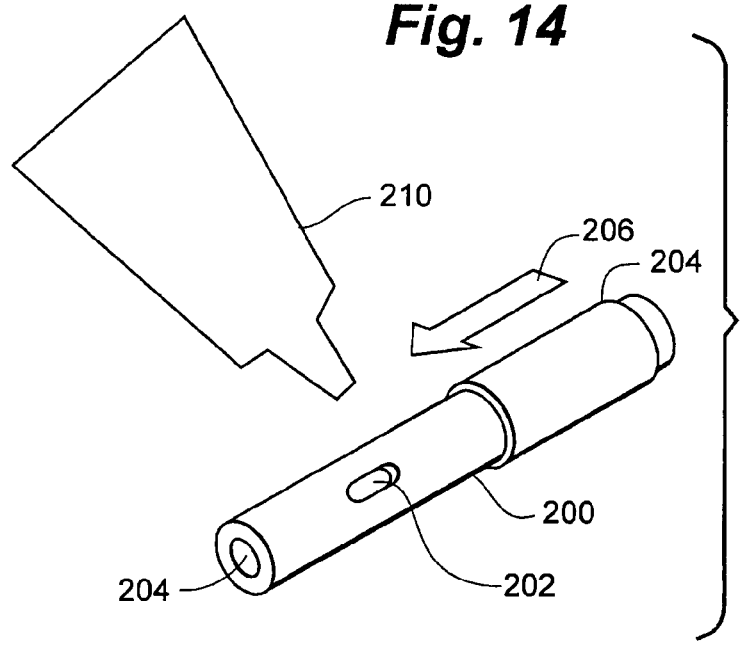
FIG. 14 is a fragmentary, highly diagrammatic, perspective view of a lead body and stylet port having a sleeve or sealer tube disposed over the lead body together with a sealant source.

FIG. 14 is a highly diagrammatic, perspective view of a lead body 200 having a port 202 in the lead body sidewall, and a central lumen 204 formed within the lead. A sleeve or sealer tube 204 is shown positioned over lead body 200. An adhesive or sealant source 210 is also illustrated. In some embodiments, a curable adhesive is used to seal the port used to provide access to the stylet lumen within the lead. In use, after the stylet has been removed from the port, a sealant or curable adhesive can be administered in or on the port. Sealer sleeve 204 can then be slid over the port now carrying the sealant, as indicated by arrow 206.

Figure 15:
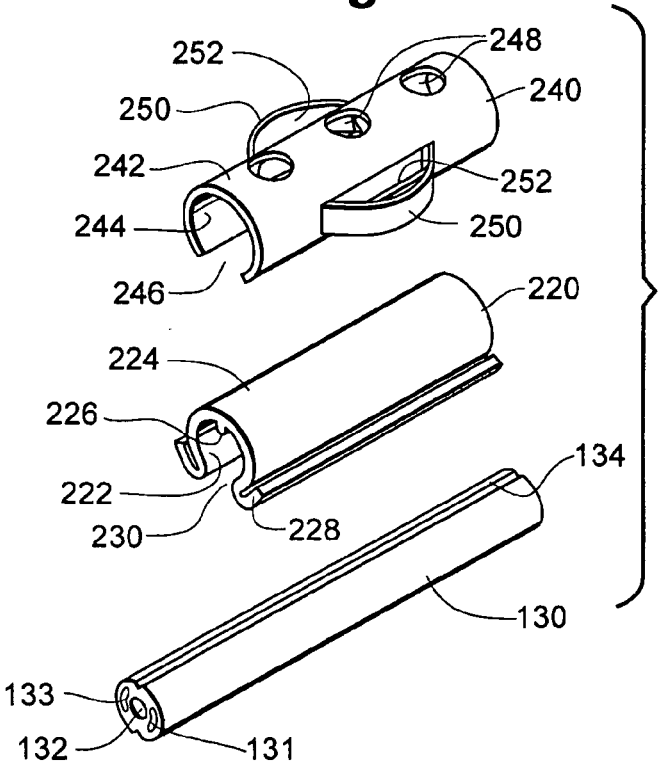
FIG. 15 is an exploded view of a sleeve assembly including a lead body, an inner sealing sleeve, and an outer sealing sleeve having wings and suture guides.

FIG. 15 illustrates lead body 130, an inner sealing sleeve 220, and an outer sealing sleeve 240. Lead body 130 includes longitudinal groove 134, which serves as an indicia of a radial position at which an inserted stylet will not contact the conductors within. Central stylet lumen 132 is as previously illustrated, with lead 130 including a first conductor lumen 131 and a second conductor lumen 133.

Inner sealing sleeve 220 is preferably formed of a polymeric material, which can be a low-durometer material. Inner sealing sleeve can include an outer surface 224, an inner surface 222, curled back portions 228, a longitudinal gap 230 having a width, and an inward protrusion 226 extending downward toward longitudinal gap 230. Inner sleeve 220 can be formed of a sealant material, which may or may not have sufficient strength by itself to form a mechanically sound seal about a stylet access port.

Outer sealing sleeve 240 is also illustrated, having a sidewall 243, an outer surface 242, an inner surface 244, and a longitudinal gap 246 having a gap width. Three holes 248 may be seen formed in the sidewall of outer sealing sleeve 240. Holes 248 may be used to apply adhesive to a port in the lead body in embodiments not utilizing an inner sleeve after the outer sealing sleeve has been put in place over the desired location. Outer sealing sleeve 240 also includes a pair of opposed wings 250 having an enclosed aperture 252 formed within each wing. Wings 250 can be used to spread apart outer sleeve 240, thereby opening the jaw-like opposed tube sections adjacent longitudinal gap 246.

Figure 16:
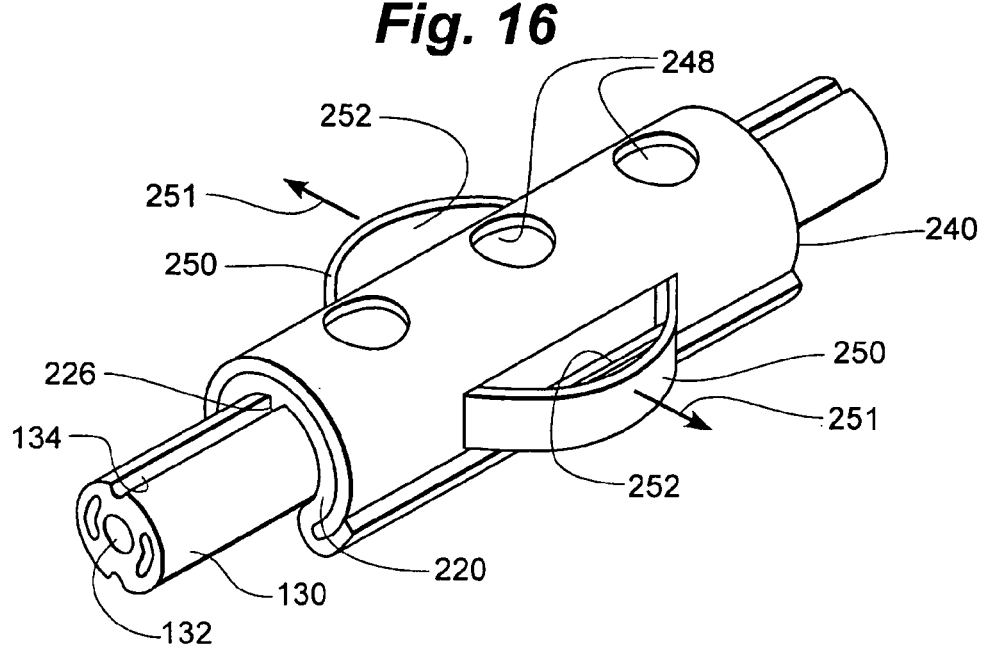
FIG. 16 is a fragmentary, perspective view of the lead body and sealing sleeves of FIG. 15, having the outer sleeve holding the inner sealing sleeve against the lead body.

FIG. 16 illustrates lead body 130, inner sealing sleeve 220, and outer sealing sleeve 240, previously discussed with respective FIG. 15. Inward protrusion 226 of inner sleeve 220 may be seen disposed within longitudinal groove 134. As previously discussed, any visual indicia of radial position on lead body 130 may be used to properly position a sealing sleeve or other device. Inner sealing sleeve 220 may be formed of a soft, low durometer material, for example, having a durometer of between about 10A and 50A (Shore A hardness). Inner sealing sleeve 220 is preferably formed of a polymeric material. Outer sealing sleeve 240 is preferably formed of a metallic material, for example, stainless steel or Nitinol. Outer sealing sleeve 240 may be seen as holding inner sealing sleeve 220 in place about the stylet access port formed into lead body 130. Holes 248 formed in the sidewall of outer sleeve 240 may be used to deposit adhesive material, for example, after outer sleeve 240 has been positioned about inner sleeve 220. The adhesive or sealant or other melted polymeric material can also be used to secure the position of outer sleeve 240 relative to inner sleeve 220.

As indicated by arrows 251, wings 250 may be pulled apart to widen the longitudinal gap and allow the inner and outer sealing sleeves 220 and 240 to be inserted over lead body 130 or removed from lead body 130. Enclosed aperture 252, within wings 250, can be used as a suture guide. Once the lead has been position within the body, and the stylet removed, the access port can be covered with inner and outer sealing sleeves 220 and 240. Outer sleeve 240 can be held in position relative to the body by running a suture through the enclosed apertures 252 and the sutures threaded through a portion of the human body in which the lead has been inserted. Outer sleeve 240 can include or be formed primarily of a radiopaque material to allow determining the position of the outer sleeve and the enclosed stylet access port at a later date.

Figure 17:
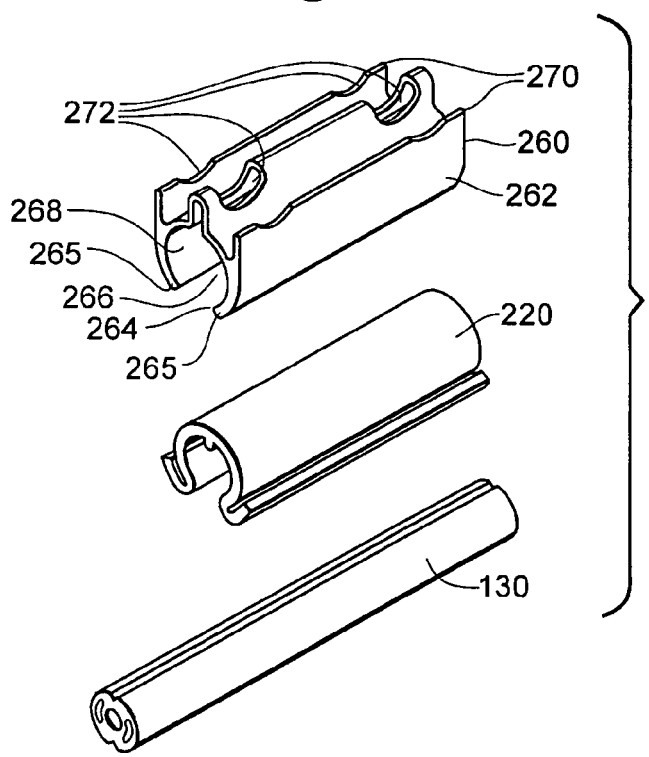
FIG. 17 is an exploded, perspective view of the lead body and inner sealing sleeve of FIG. 15, and an outer sealing sleeve having suture guides and wings for opening the outer sleeve to receive the lead body.

FIG. 17 illustrates lead body 130 and inner sealing sleeve 220 as previously described. An outer sealing sleeve 260 may be seen, having a body 262 including an inner surface 268 defining a longitudinal channel 266 within. A longitudinal gap 264 may be seen, having a gap width. Body 262 may be seen forming a pair of opposed jaws 265 on either side of the longitudinal gap. Opposite of gap 264 and jaws 265 may be seen a pair of opposed wings or arms 270. Additionally, external concavities 272 may be seen, which can be used as suture guides as previously discussed with respect to FIG. 16.

Figure 18:
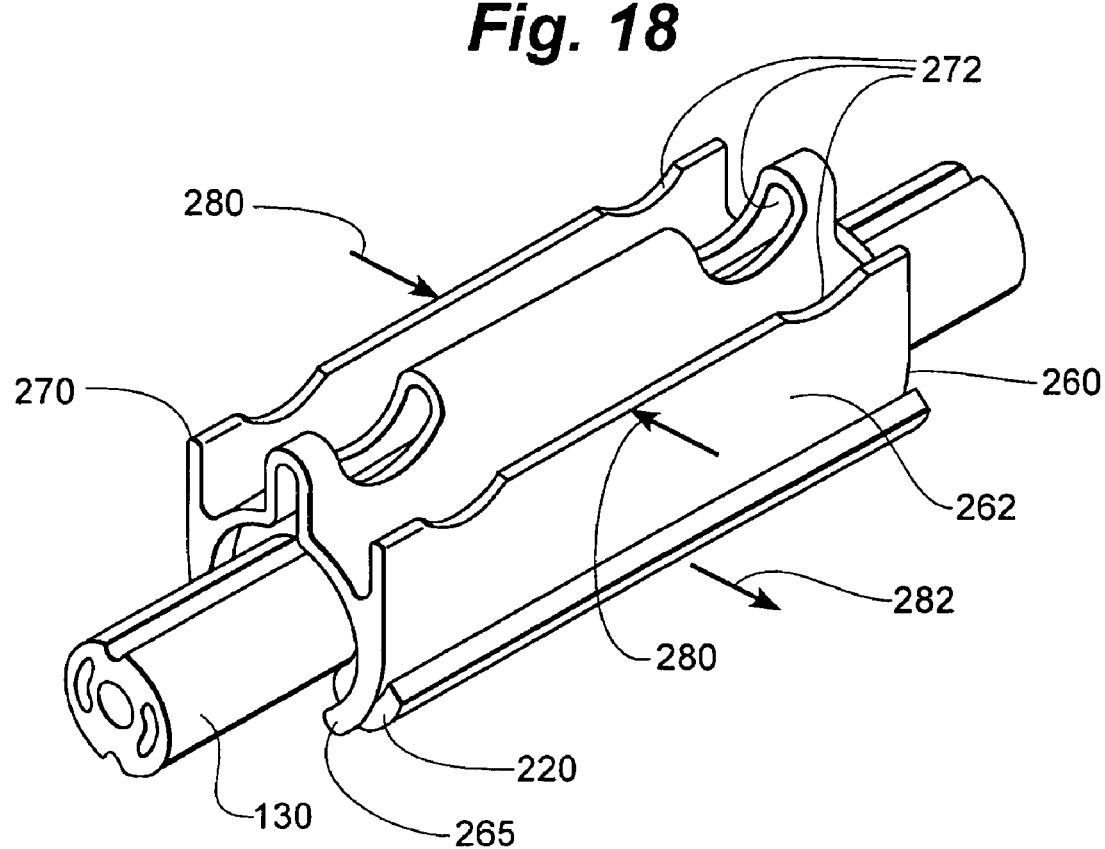
FIG. 18 is a fragmentary, perspective view of the sealing sleeve of FIG. 7, shown disposed over the lead body of FIG. 7.

FIG. 18 illustrates lead body 130, inner sleeve 220 and outer sealing sleeve 260, as previously described with respect to FIG. 17. FIG. 18 more illustrates external concavities 272, which may also be seen extending through outer sleeve body 262. If desired, the through holes can also be used as suture guides. As indicated by arrows 280 and 282, squeezing opposed wings 270 can force apart jaws 265, thereby increasing the width of the longitudinal gap. This can allow advancing the inner and outer sleeves over a lead body, or removing the inner and outer sleeves from the lead body. As discussed with respect to FIG. 16, the inner and outer sleeves can be disposed over the stylet port after the stylet has been removed. Sutures can be run through the suture guides and sutured into place in the patient, as desired.

The foregoing detailed description should be read with reference to the drawings, in which like elements in different drawings are numbered identically. The drawings, which are not necessarily to scale, depict selected embodiments and are not intended to limit the scope of the invention. Several forms of invention have been shown and described, and other forms will now be apparent to those skilled in art. It will be understood that embodiments shown in drawings and described above are merely for illustrative purposes, and are not intended to limit scope of the invention as defined in the claims that follow.

What is claimed is:

1. An implantable lead comprising:
    an elongate lead body comprising a proximal region, a distal region, and an intermediate region disposed between the proximal and distal regions;
    means for providing electrical continuity between the proximal and distal regions comprising a plurality of proximal electrical contacts electrically coupled to a plurality of distal electrical contacts; and
    means for reversibly stiffening the lead between the intermediate and distal regions while not stiffening the lead between the intermediate and proximal regions comprising means for receiving a stiffening member into the lead body for disposition between the intermediate region and the distal region, wherein the means for receiving a stiffening member includes means for indicating a radial position on the lead body at which a sharp member inserted into the lead body will not contact the means for providing electrical continuity.

2. An implantable lead as in claim 1, further including means for indicating a position on the lead body at which a port can be formed in the lead body to connect with the means for receiving a stiffening member without contacting the means for providing electrical continuity.

3. An implantable lead as in claim 2, wherein the means for providing electrical continuity comprises a plurality of proximal electrical contacts electrically coupled to a plurality of distal electrical contacts, wherein the means for receiving a stiffening member is disposed between the innermost of the proximal and distal contacts.

4. An implantable lead as in claim 2, further comprising means for radiopaquely marking and sealing the means for receiving the stiffening member.

5. An implantable lead as in claim 2, wherein the means for receiving a stiffening member further comprises means for guiding the stiffening member into the lead body.

6. An implantable lead as in claim 5, wherein the means for guiding the stiffening member into the lead body includes means for distally directing the stiffening member into the lead body.

7. An implantable lead as in claim 1, further comprising means for radiopaquely marking the lead intermediate region.

8. An implantable lead as in claim 1, wherein the lead has an outer diameter of less than about 1 millimeter and a total length of between about 10 cm. and about 150 cm.

9. A method for inserting an implantable lead into the human body, the method comprising:
    providing an elongate stiffening member having a proximal region and a distal region;
    providing an elongate lead body comprising: a proximal region, a distal region, an intermediate region disposed between the proximal and distal regions, and a sidewall; at least one conductor disposed within the lead body and extending from the lead body proximal region to the lead body distal region; at least one proximal contact disposed in the lead body proximal region and in electrical contact with the at least one conductor; at least one distal contact disposed in the lead body distal region and in electrical contact with the at least one conductor; a lumen disposed through the lead body between the lead body distal region and the lead body intermediate region; and a port providing access between the lead body sidewall and the lumen in the lead body intermediate region, wherein the port and lumen are dimensioned to slidably receive the elongate stiffening member,
    inserting the lead distal region into the human body while carrying the stiffening member at least partially within the lumen between the port and the lead distal region,
    inserting the stiffening member into the lead through the lead port before inserting the lead distal region into the human body
    retracting the stiffening member from the inserted lead distal region, and
    sealing the port after retracting the stiffening member by sliding a sealing sleeve over the port.

10. A method as in claim 9, in which the sleeve includes at least one suture guide, the method further comprising suturing the sleeve to the human body using a suture secured to the suture guide.

11. A method for inserting an implantable lead into the human body, the method comprising:
    providing an elongate stiffening member having a proximal region and a distal region;
    providing an elongate lead body comprising: a proximal region, a distal region, an intermediate region disposed between the proximal and distal regions, and a sidewall; at least one conductor disposed within the lead body and extending from the lead body proximal region to the lead body distal region; at least one proximal contact disposed in the lead body proximal region and in electrical contact with the at least one conductor; at least one distal contact disposed in the lead body distal region and in electrical contact with the at least one conductor; a lumen disposed through the lead body between the lead body distal region and the lead body intermediate region; and a port providing access between the lead body sidewall and the lumen in the lead body intermediate region, wherein the port and lumen are dimensioned to slidably receive the elongate stiffening member, inserting the lead distal region into the human body while carrying the stiffening member at least partially within the lumen between the port and the lead distal region, inserting the stiffening member into the lead through the lead port before inserting the lead distal region into the human body retracting the stiffening member from the inserted lead distal region, and sealing the port after retracting the stiffening member by sliding a sealing sleeve over the port by applying a sealant to the port and the sealant, includes a curable sealant material and the sealing includes allowing the curable sealant to cure.

12. A method for inserting an implantable lead into the human body, the method comprising:

providing an elongate stylet having a proximal region and a distal region;

providing an elongate lead body comprising: a proximal region, a distal region, an intermediate region disposed between the proximal and distal regions, and a sidewall; at least one conductor disposed within the lead body and extending from the lead body proximal region to the lead body distal region; at least one proximal contact disposed in the lead body proximal region and in electrical contact with the at least one conductor; at least one distal contact disposed in the lead body distal region and in electrical contact with the at least one conductor, a lumen disposed through the lead body between the lead body distal region and the lead body intermediate region; wherein the lumen is dimensioned to slidably receive the elongate stylet;

inserting the stylet through the lead body sidewall into the lumen in the lead body intermediate region at an indicia of radial position on the lead so that the stylet inserted into the lead body will not contact the conductor; and inserting the lead distal region into the human body while carrying the stylet at least partially within the lumen.

13. A method as in claim 12, further comprising providing a hole forming guide having a channel formed through the guide, providing an elongate member having a sharp distal end dimensioned to be slidably received within the channel, the method further including disposing the hole forming guide against the lead body and advancing the elongate member sharp distal end through the channel to form a port providing access between the lead body sidewall and the lumen in the lead body intermediate region, wherein the stylet inserting is performed through the port.

14. A method as in claim 13, in which the lead body indicia includes a depression formed into the lead body, and in which the hole forming guide includes a protrusion, the method further comprising aligning the protrusion with the depression.

15. A method as in claim 12, further comprising providing a hole forming device including a body adapted to fit over the lead body, in which the hole forming device body includes a sharp inwardly protruding member and a channel extending through the body and sharp inwardly protruding member, the method further comprising urging the hole forming device sharp member into the lead body to form a port providing access between the lead body sidewall and the lumen, wherein the-stylet inserting is performed through the port.

16. A method as in claim 12, in which the indicia includes a depression in the lead body, wherein the inserting the stylet into the lead body includes inserting the stiffening member into the depression.

17. A method for inserting an implantable lead into the human body as in claim 16, further comprising providing a sealing sleeve slidably disposed over the lead body, and retracting the stylet from the inserted lead distal region to expose a port providing access between the lead body sidewall and the lumen, and sliding the sealing sleeve over the port.

18. An implantable lead comprising:

an elongate lead body comprising a proximal region, a distal region, an intermediate region disposed between the proximal and distal regions, and a sidewall;

at least one conductor disposed within the lead body and extending from the proximal region to the distal region;

at least one proximal contact disposed in the lead body proximal region and in electrical contact with the at least one conductor, at least one distal contact disposed in the lead body distal region and in electrical contact with the at least one conductor, a lumen disposed through the lead body between the distal region and the intermediate region; and an indicia of a radial position on the lead body at which a stylet inserted into the lead body will not contact the conductor.

19. An implantable lead as in claim 18, in which the indicia of radial position is a depression into the lead body.

20. An implantable lead as in claim 19, in which the indicia of radial position is a longitudinal groove.

21. An implantable lead as in claim 18, wherein the lead lumen is a central longitudinal lumen, in which the indicia marks a position where the conductor is not disposed between the indicia and the central longitudinal lumen.

22. An implantable lead assembly comprising:

an elongate stiffening member having a proximal region and a distal region;

an elongate lead body comprising a proximal region, a distal region, an intermediate region disposed between the proximal and distal regions, and a sidewall;

at least one conductor disposed within the lead body and extending from the lead body proximal region to the lead body distal region;

at least one proximal contact disposed in the lead body proximal region and in electrical contact with the at least one conductor;

at least one distal contact disposed in the lead body distal region and in electrical contact with the at least one conductor;

a lumen disposed through the lead body between the lead body distal region and the lead body intermediate region;

wherein the lumen is dimensioned to slidably receive the elongate stiffening member; and a hole forming device including a body adapted to fit over the lead body, in which the hole forming device body includes a first channel therethrough forming an angle less than 60 degrees with the lead body longitudinal center axis.

23. An implantable lead assembly as in claim 22, in which the hole forming device includes an inwardly directed longitudinal protrusion.

24. An implantable lead assembly as in claim 22, further comprising an elongate member having a sharp distal end, the member adapted to be received through the first channel to form a hole through the lead body into the lead lumen.

25. An implantable lead assembly as in claim 22, in which the hole forming device body includes a sharp inwardly directed member, in which the first channel extends through the hole forming device body and through the inwardly directed sharp member, the first channel forming an angle less than 60 degrees with the lead body longitudinal center axis.

26. An implantable lead assembly as in claim 25, further comprising a stylet sized and dimensioned to be received through the hole forming device first channel and adapted to be received by the lead lumen through the hole formed by the sharp inwardly directed member.

* * * * *